US010981161B2

(12) United States Patent
Miyaji et al.

(10) Patent No.: US 10,981,161 B2
(45) Date of Patent: Apr. 20, 2021

(54) METHOD FOR PRODUCING PALLADIUM-GOLD LOADED CATALYST FOR VINYL ACETATE SYNTHESIS

(71) Applicant: N.E. CHEMCAT CORPORATION, Minato-ku (JP)

(72) Inventors: Takayuki Miyaji, Tokyo (JP); Hayato Miyazaki, Tokyo (JP)

(73) Assignee: N.E. CHEMCAT CORPORATION, Minato-ku (JP)

(*) Notice: Subject to any disclaimer, the term of this patent is extended or adjusted under 35 U.S.C. 154(b) by 0 days.

(21) Appl. No.: 16/620,193

(22) PCT Filed: Jun. 14, 2018

(86) PCT No.: PCT/JP2018/022668
§ 371 (c)(1),
(2) Date: Dec. 6, 2019

(87) PCT Pub. No.: WO2018/235705
PCT Pub. Date: Dec. 27, 2018

(65) Prior Publication Data
US 2020/0094237 A1    Mar. 26, 2020

(30) Foreign Application Priority Data

Jun. 23, 2017   (JP) .............................. JP2017-123030
Jun. 23, 2017   (JP) .............................. JP2017-123182

(51) Int. Cl.
    *B01J 35/08*        (2006.01)
    *B01J 37/02*        (2006.01)
    (Continued)

(52) U.S. Cl.
    CPC ........... *B01J 37/0205* (2013.01); *B01J 21/08* (2013.01); *B01J 23/66* (2013.01); *B01J 35/023* (2013.01);
    (Continued)

(58) Field of Classification Search
    CPC ........ B01J 37/0205; B01J 21/08; B01J 23/66; B01J 35/023; B01J 35/08; B01J 35/1014;
    (Continued)

(56) References Cited

U.S. PATENT DOCUMENTS

| 5,347,046 A | 9/1994 | White et al. |
| 2010/0022796 A1 | 1/2010 | Heidenreich et al. |

FOREIGN PATENT DOCUMENTS

| CN | 104549517 A | 4/2015 |
| JP | 60-9864 B2 | 3/1985 |

(Continued)

OTHER PUBLICATIONS

International Search Report dated Aug. 28, 2018 in PCT/JP2018/022668 filed on Jun. 14, 2018, 2 pages.

(Continued)

*Primary Examiner* — Haytham Soliman
(74) *Attorney, Agent, or Firm* — Oblon, McClelland, Maier & Neustadt, L.L.P.

(57) ABSTRACT

The present invention provides a technique capable of adjusting the loading positions of gold and palladium in a VAM catalyst by a method of producing a palladium-gold loaded catalyst for vinyl acetate synthesis. The method includes a step of impregnating a spherical porous molded carrier of an inorganic oxide with a mixed aqueous solution containing a palladium precursor as a catalytically active species and a gold precursor as a co-catalyst component, and subsequently impregnating the resultant spherical porous molded carrier with an aqueous alkaline solution to water-insolubilize the palladium precursor and the gold precursor in the spherical porous molded carrier to obtain a palladium-gold immobilized spherical porous molded carrier; and a (Continued)

subsequent step of adjusting the moisture content of the palladium-gold immobilized spherical porous molded carrier.

8 Claims, 4 Drawing Sheets

(51) Int. Cl.
*B01J 21/08* (2006.01)
*B01J 23/66* (2006.01)
*B01J 35/02* (2006.01)
*B01J 35/10* (2006.01)
*B01J 37/03* (2006.01)
*B01J 37/08* (2006.01)
*B01J 37/18* (2006.01)
*C07C 67/055* (2006.01)

(52) U.S. Cl.
CPC ............ *B01J 35/08* (2013.01); *B01J 35/1014* (2013.01); *B01J 35/1019* (2013.01); *B01J 35/1023* (2013.01); *B01J 37/035* (2013.01); *B01J 37/08* (2013.01); *B01J 37/18* (2013.01); *C07C 67/055* (2013.01)

(58) Field of Classification Search
CPC .. B01J 35/1019; B01J 35/1023; B01J 37/035; B01J 37/08; B01J 37/18; B01J 23/58; B01J 37/02; C07C 67/055; C07C 69/15; C07B 61/00
USPC ........................................................... 502/10
See application file for complete search history.

(56) References Cited

FOREIGN PATENT DOCUMENTS

| | | |
|---|---|---|
| JP | 8-510685 A | 11/1996 |
| JP | 2002-45706 A | 2/2002 |
| JP | 2010-512985 A | 4/2010 |
| JP | 2010-527778 A | 8/2010 |
| WO | WO-0136091 A1 * 5/2001 .............. B01J 23/52 |
| WO | WO 2016/198561 A1 | 12/2016 |

OTHER PUBLICATIONS

Ohmaye, "Review on Synthetic Methods of Vinyl Acetate.", 1987, vol. 45, No. 7, pp. 691-700.

Nakamura et al., "Historical Development of Vinyl Acetate Manufacturing Processes", 1976, vol. 34, No. 12, pp. 969-979.

* cited by examiner

METHOD FOR PRODUCING PALLADIUM-GOLD LOADED CATALYST FOR VINYL ACETATE SYNTHESIS

FIELD OF INVENTION

The present invention relates to a method of producing a palladium-gold loaded catalyst for vinyl acetate synthesis, which catalyst is used in synthesis of vinyl acetate using acetic acid, ethylene, and oxygen as raw materials.

BACKGROUND OF ART

Vinyl acetate is an important industrial material which is used as a raw material of a vinyl acetate resin, a raw material of polyvinyl alcohol, as well as a monomer for copolymerization with ethylene, styrene, acrylate, methacrylate, or the like, in paint, adhesive, fiber treating agent, or other various fields.

For production of vinyl acetate using acetic acid, ethylene, and oxygen as raw materials, there has long been known a catalyst in which palladium and gold are skin-loaded in a surface layer of a porous molded carrier (surface layer-biased loading) and, as required, an alkali metal is further loaded therein using potassium acetate or the like (NPLs 1 and 2). Such a catalyst is actively studied even now (PTL 1, 2). In the present invention, vinyl acetate is sometimes referred to simply as "VAM" and a catalyst for producing VAM is sometimes referred to simply as a "VAM catalyst".

Gold in a VAM catalyst plays a roll of suppressing sintering of palladium which functions as active points and of enhancing the selectivity in synthesis of vinyl acetate. Potassium is known to function as a co-catalyst and an activator (PTLs 2 and 3). However, in catalysts obtained by existing methods, no detailed study has been made on optimal distributions of palladium and gold.

In light of the actions of palladium and gold as described above, a VAM catalyst preferably has distributions of palladium and gold that is matched with each other on the surface of a carrier. As a technique for achieving such distributions, PTL 2 proposes a method in which a carrier is impregnated with an aqueous alkaline solution for immobilization of palladium and gold, and then impregnated with a palladium salt solution and a gold solution, thereby forming a shell-type catalyst, and the method achieves high performance.

Improvement in catalytic performance by loading gold together with palladium as described above seemingly conflicts with the nature of gold with a low catalytic activity. However, gold, which has a low activity, is stably present even in a reactive system. Thus, when existing together with palladium, gold has an effect of suppressing denaturation, such as sintering, of palladium in a reactive system to prolong the lifetime of a catalyst. In addition, suppression of sintering leads to maintenance of high dispersion of palladium in a carrier. Maintenance of high dispersion results in maintenance of high catalytic activity. In other words, it is a desired that gold in a catalyst for producing vinyl acetate be loaded in a matched state in a shell layer (skin layer) of a carrier in which palladium is loaded.

On the other hand, there is concern that a high activity of a VAM catalyst due to palladium causes unintended side reactions. The conditions of production of VAM for industrial use vary from a person skilled in the art to another. Examples of such conditions include a high partial pressure of oxygen and a low flow rate of a reactant per unit volume of the catalyst, where there is concern that the reaction may be excessively promoted. For this reason, a catalyst in which side reactions are suppressed is also needed. As such a catalyst in which side reactions can be suppressed, a catalyst in which the distribution and concentration of gold are adjusted is conceived as disclosed in PTL 4 (claim 25). For example, in a carrier in which palladium and gold are loaded, the gold concentration is set to be high in the outside of the carrier and low in the inside thereof. Accordingly, in the surface side of a carrier, i.e., in a portion to be exposed to a high partial pressure of oxygen (a portion where the activity is easily increased), side reactions are suppressed and sintering due to the high activity of palladium can be suppressed. Meanwhile in the inside of a carrier, i.e., in a portion to be exposed to a low partial pressure of oxygen (a portion where the activity is hardly increased but side reactions are less likely to occur), the palladium concentration can be increased to achieve a high conversion. If a catalyst can be designed in this manner, a high conversion and a high selectivity can be achieved as the whole catalyst particle. However, in an example as in PTL 4 (claim 12), the process for producing a catalyst is complicated and is not an industrially advantageous production method.

In addition, with a trend toward the green chemistry in recent years, the market increasingly requires further improvement also in the activity of a VAM catalyst, i.e., the yield and selectivity thereof.

CITATION LIST

Patent Literature

PTL 1: JP-T-2010-527778 (the term "JP-T" as used herein means a published Japanese translation of a PCT patent application.)
PTL 2: JP-T-H08-510685
PTL 3: JP-B-S60-9864
PTL 4: JP-A-2002-45706

Non-Patent Literature

NPL 1: "Sakusan Biniru Seizo no Kako, Genzai, soshite Mirai (Past, present, and future situation of vinyl acetate production)" Yuki Gosei Kagaku (Journal of Synthetic Organic Chemistry, Japan) Vol. 45, No. 7 (1987) 691-700
NPL 2: "Sakusan Biniru Seizo Gijutu no Hensen (Change in vinyl acetate production technique)", Yuki Gosei Kagaku (Journal of Synthetic Organic Chemistry, Japan) Vol. 34, No. 12 (1976) 969-979

SUMMARY OF INVENTION

Technical Problem

An object of the present invention is to provide a technique capable of easily adjusting the loading positions of gold and palladium in a VAN catalyst to meet the industrial need.

Solution to Problem

As a result of intensive studies, the present inventors have found that the loading positions of gold and palladium in a VAM catalyst can be easily adjusted by impregnating a spherical porous molded carrier formed of an inorganic oxide with a mixed aqueous solution that contains a palladium precursor serving as a catalytically active species and a gold precursor serving as a co-catalyst component, and subsequently impregnating the resultant spherical porous molded carrier with an aqueous alkaline solution to thereby water-insolubilize the palladium precursor and the gold precursor in the spherical porous molded carrier, thus obtaining a palladium-gold immobilized spherical porous molded carrier, and subsequently adjusting the moisture content of the palladium-gold immobilized spherical porous molded carrier, thus completing the present invention.

Specifically, the present invention provides a method of producing a palladium-gold loaded catalyst for vinyl acetate synthesis, the method including:
a step of impregnating a spherical porous molded carrier formed of an inorganic oxide with a mixed aqueous solution that contains a palladium precursor serving as a catalytically active species and a gold precursor serving as a co-catalyst component, and subsequently impregnating the resultant spherical porous molded carrier with an aqueous alkaline solution to thereby water-insolubilize the palladium precursor and the gold precursor in the spherical porous molded carrier, thus obtaining a palladium-gold immobilized spherical porous molded carrier; and a step of subsequently adjusting a moisture content of the palladium-gold immobilized spherical porous molded carrier.

The present invention also provides a method of adjusting the loading positions of palladium and gold in a palladium-gold loaded catalyst for vinyl acetate synthesis, the method including:
a step of impregnating a spherical porous molded carrier formed of an inorganic oxide with a mixed aqueous solution that contains a palladium precursor serving as a catalytically active species and a gold precursor serving as a co-catalyst component, and subsequently impregnating the resultant spherical porous molded carrier with an aqueous alkaline solution to thereby water-insolubilize the palladium precursor and the gold precursor in the spherical porous molded carrier, thus producing a palladium-gold immobilized spherical porous molded carrier; and a step of subsequently adjusting a moisture content of the palladium-gold immobilized spherical porous molded carrier.

Advantageous Effects of Invention

According to the present invention, loading positions of gold and palladium in a VAM catalyst can be easily adjusted without any specific apparatus or complicated steps.

When a VAM catalyst in which the loading positions of gold and palladium are matched to the outer shell side of the spherical porous molded carrier is produced by the present invention, the VAM catalyst is expected to have increased catalytic performance due to the use of gold.

In addition, when a VAM catalyst that has a higher gold concentration in the surface side of a palladium load area, the area being given by palladium biasedly loaded in the outer shell side of a spherical porous molded carrier, and that has a lower gold concentration in the inside of the same area is produced by the present invention, the VAM catalyst has a high conversion and a high selectivity due to the effective location of gold.

DESCRIPTION OF EMBODIMENTS

Spherical Porous Molded Carrier

A carrier used in the method of producing a palladium-gold loaded catalyst for vinyl acetate synthesis of the present invention (hereinafter referred to as "the production method of the present invention") is a spherical porous molded carrier and is formed of a porous inorganic oxide. A carrier that is porous can load palladium to be loaded in a highly dispersed manner and thus is expected to effect a highly active catalytic reaction. Due to the inorganic oxide, the state in a catalytic reaction system is stable. Due to the spherical shape, the depth of impregnation with catalyst components and precursors thereof can be easily controlled. A catalyst in which the load widths of catalytic components, such as palladium and gold, are constant for each component has a uniform reaction activity on the catalyst surface and even in an industrial application, the reaction conditions can be easily set.

Such a spherical porous molded carrier preferably has a diameter of 3 to 7 mm and more preferably 4 to 6 mm. As a spherical porous molded carrier for a catalyst, there is a carrier having a smaller size, but a relatively large carrier ensures an enough space to allow reactants to flow when the catalyst is charged in a reactor in use, facilitating an efficient reaction with low pressure loss in the reaction. However, a larger void space between catalyst particles is not always good, and a catalyst having a too large void space, namely a catalyst having a too large particle size leads to a low geometric surface area (the surface area of the spheres) per unit volume in the catalyst and when used as a catalyst, a sufficient activity is not achieved in some cases.

The spherical porous molded carrier used in the production method of the present invention has a porous structure and the state can also be represented by the specific surface area (BET value). Specifically, the BET value is preferably 10 to 1000 $m^2/g$, more preferably 50 to 500 $m^2/g$, and most preferably 100 to 300 $m^2/g$. A carrier having such a BET value can support palladium and gold in a highly dispersed manner and thus the actions of the palladium component and the gold component according to the method of the present invention can be easily exhibited.

In the production method of the present invention, the amount of water in the spherical porous molded carrier impregnated with catalyst components can be represented as a moisture content. The moisture content can be specified by a method referring "JIS R 22051992, Testing Method for Apparent Porosity, Water Absorption, Specific Gravity of Refractory Bricks". In the present invention, a spherical porous molded carrier is dried, and the moisture content is determined from the mass of the contained water based on the mass of the dry carrier. Note that the water absorption in a spherical porous molded carrier impregnated with no catalyst component is similarly determined from the mass of the contained water based on the mass of the dry carrier.

The method of measuring a mass of water to be contained in a spherical porous molded carrier impregnated with catalyst components is not limited but the mass can be determined as follows. 50 g of the spherical porous molded carrier is fully immersed in ion exchange water for 30 minutes or longer, and is taken out onto paper towel and the carrier is rolled thereon to remove the excess water on the carrier surface. The difference between the mass of the resultant carrier and the mass measured after drying the carrier containing water at 105° C. for 8 hours is taken as the amount of water that the carrier can contain. The mass of water to be contained can be determined based on the above value. A water absorption in the present invention can also be determined from a value measured in the same manner. The water absorption in the completely water-absorbing state is referred to as saturated water absorption. The saturated water absorption is preferably 0.2 to 2 [g/g] and more preferably 0.4 to 1 [g/g].

Palladium

The palladium component used in the production method of the present invention is preferably a water soluble palladium salt since a spherical porous molded carrier is impregnated with an aqueous solution thereof. The palladium salt is not limited and is appropriately selected according to a combination with an alkaline solution which is to be used for water-insolubilizing a gold compound as described later and the palladium salt to immobilize the components.

Examples of such palladium salts include palladium chloride, palladium nitrate, palladium sulfate, sodium chloropalladate, potassium chloropalladate, and palladium acetate. A particularly preferred example is sodium chloropalladate which is used in the form of an aqueous solution. The concentration of the aqueous palladium compound solution is not limited, but is preferably 1 to 50% by weight and more preferably 2 to 25% by weight.

Gold

The gold component used in the production method of the present invention is also preferably a water soluble gold salt since a spherical porous molded carrier is impregnated with an aqueous solution thereof as with a palladium component. The gold salt is also appropriately selected according to a combination with an alkaline solution which is to be used for water-insolubilizing the gold salt to immobilize the component as with the palladium salt.

Examples of such water soluble gold salts include, but not limited to, chloroauric acid, sodium chloroaurate, and potassium chloroaurate, and a preferred example is chloroauric acid which is used in the form of an aqueous solution. The concentration of such an aqueous gold compound solution is not limited, but is preferably 1 to 50% by weight and more preferably 2 to 25% by weight as with the aqueous palladium compound solution described above.

Aqueous Alkaline Solution

The aqueous alkaline solution used in the production method of the present invention is not limited as long as a palladium salt solution and a gold salt solution can be immobilized in the water-insoluble state on the outer shell side of a spherical porous carrier in the preceding step. Such immobilization can be considered as precipitation on the surface side of the carrier.

Examples of components of such aqueous alkaline solutions include alkaline compounds, such as hydroxides of alkali metals and alkaline earth metals, bicarbonates of alkali metals and alkaline earth metals, carbonates of alkali metals and alkaline earth metals, and silicates of alkali metals and alkaline earth metals. As an alkali metal, lithium, sodium, potassium, or cesium is used. As an alkaline earth metal, magnesium, calcium, strontium, or barium is used. Sodium metasilicate, potassium metasilicate, sodium hydroxide, or potassium hydroxide is suitably used. With respect to the amount of such an aqueous alkaline solution component, i.e., the amount of the alkaline component used in terms of solid content, since such an aqueous alkaline solution in the present invention is used for the purpose of immobilization (precipitation in a spherical porous molded carrier) of a palladium component or a gold component as described above, the aqueous alkaline solution is preferably used after adjusting the concentration so that the amount of the alkali is a little excess relative to the amount of that to be consumed for water-insolubilizing the palladium salt and the gold salt. Note that the excess aqueous alkaline solution component is preferably removed from the spherical porous molded carrier by a water washing step or the like.

Impregnation with Aqueous Palladium Salt Solution and Aqueous Gold Salt Solution In the production method of the present invention, a spherical porous molded carrier is impregnated with an aqueous palladium salt solution and an aqueous gold salt solution. The impregnation here may be impregnation with a mixed aqueous solution in which an aqueous palladium salt solution and an aqueous gold salt solution are mixed.

In the production method of the present invention, a technique of impregnating a spherical porous molded carrier with an aqueous alkaline solution, an aqueous palladium salt solution, or an aqueous gold salt solution is not limited and the impregnation may be performed by shaking a rotating cylindrical drum container containing a carrier and manually spraying the solution with a sprayer or may be performed by immersing a spherical porous molded carrier contained in a container through which a solution can flow, such as a mesh bag, in a solution having a previously adjusted concentration. The technique of spraying with a sprayer can control the amount of impregnation in a relatively correct manner and the technique of immersion is suited to a mass production due to its simple operation. The techniques for impregnation may be selected alone or may be used in combination depending on the process and production equipment.

Step of Adjusting Moisture Content of Palladium-Gold Immobilized Spherical Porous Molded Carrier In the production method of the present invention, the method of adjusting the moisture content of the palladium-gold immobilized spherical porous molded carrier obtained in the foregoing manner is not limited but, for example, the moisture content may be adjusted by replenishing water to the palladium-gold immobilized spherical porous molded carrier or drying the palladium-gold immobilized spherical porous molded carrier. Note that, since a spherical porous molded carrier is preferably uniformly impregnated with an aqueous alkaline solution, an aqueous palladium salt solution, or an aqueous gold salt solution, the method of adjusting the moisture content is preferably a method in which a drying step is applied after impregnating the carrier with solutions of components in such an amount that the carrier can absorb. Hereinafter, a spherical porous molded carrier impregnated with an aqueous alkaline solution, an aqueous palladium salt solution, or an aqueous gold salt solution is sometimes referred to simply as an "impregnated carrier". In this case, the temperature and the time may be adjusted. By adjusting at least the moisture content, the loading positions of palladium and gold in a palladium-gold immobilized spherical porous molded carrier can be adjusted.

Condition for Matching Loading Positions of Palladium and Gold

In the production method of the present invention, when an aging step as described below is performed with a moisture content of 4% by weight or more and desirably 5 to 50% by weight based on the weight of a spherical porous molded carrier as described above, the distributions of palladium and gold can be matched better.

Aging Step

In the production method of the present invention, when the impregnated carrier is subjected to an aging step, the temperature is preferably 40 to 120° C. and preferably 50 to 80° C. With a too low temperature, aging proceeds significantly slowly and thus the method is not industrially available. With a too high temperature, water easily vaporizes from the impregnated carrier and it is difficult to maintain the amount of water needed for aging or it is required to use an airtight container for suppressing water vaporization. When aging is performed at a high temperature using an airtight container, there arises concern about break of the container or mist spout upon releasing the system.

Under such a temperature and a moisture content as described above, the impregnated carrier is aged for 72 hours or more. With a too short aging time, it is difficult to match the loading positions of palladium and gold. A long aging time is less likely to have influence on the distributions of palladium and gold, but a too long time leads to difficult maintenance of the amount of water of the water-impregnated carrier or high production cost due to the prolonged process. From the above reasons, an aging time of 168 hour is sufficient to match the distributions of palladium and gold.

Condition of Biasedly Loading Palladium and Gold (not Matching the Loading Positions of Palladium and Gold)

In the production method of the present invention, if the condition for matching the loading positions of palladium and gold is not met, palladium and gold can be loaded in biased locations. Examples of such conditions include a condition in which the foregoing moisture content is not met and a condition in which no aging step is performed. More specifically, for example, the moisture content may be made less than 4% by weight, the temperature may be maintained less than 40° C., or the next step may be performed within 72 hours, so that the catalyst is not aged.

Reduction Step

A reduction treatment is preferably performed after the moisture content is adjusted (followed by further aging, as needed) in the foregoing manner. With this step, palladium and gold in the VAM catalyst are securely reduced.

In order to convert the spherical porous molded carrier in which palladium and gold are loaded obtained by the production method of the present invention to a palladium-gold loaded catalyst for vinyl acetate synthesis, the carrier is subjected to a reduction treatment without aging after water-insolubilization with an aqueous alkaline solution. By the reduction treatment, a layer loading a palladium component is completely immobilized in a metal state in which the concentration of a gold component is high in the outer shell side of the spherical porous molded carrier and low in the inside thereof. Such a distribution of gold has been already achieved at the time when the gold component is water-insolubilized by an aqueous alkaline solution, but before the reduction, the gold component may move through aging and the loading positions of palladium and gold may be matched. In this manner, a catalyst is obtained in which an action of adjusting the partial pressure of oxygen in the catalyst is exhibited by gold used for maintaining the dispersion state of palladium.

The means for the reduction treatment in the production method of the present invention is not limited, and a means is appropriately selected from techniques that are widely used in production of catalysts. However, when a liquid is used as a reductant, hydrazine, formic acid, sodium borohydride, or any alcohol can be used, and when a gas is used, hydrogen, ethylene, or the like can be used.

As the reduction means in the production method of the present invention, a gaseous phase reduction method using hydrogen as a reducing component is preferred. In the case of liquid reduction, since the reduction proceeds in a solvent, a precious metal component easily moves in the course of the reduction, a precious metal is likely to aggregate, and the loaded precious metal particles are likely to be enlarged. However, there may be concern about sintering of fine precious metal particles due to long-term use depending on the conditions of the VAM production. Thus, a certain degree of precious metal particle size in the early stage of the use of a VAM catalyst may be advantageous in the case where the activity is required to hardly change from the time immediately after the production to keep constant performance for the long period of time. In contrast, in a gas phase reduction method, since the reduction proceeds quickly and no solvent intermediates, a precious metal component is unlikely to move in the reduction process and precious metal particles can be loaded in a highly dispersed state. When a precious metal is in a highly dispersed state, the surface area per unit mass of the precious metal particles is increased, and a catalyst having a large active face can be obtained.

Such a load state of precious metal particles can be represented by the surface area per unit mass of the precious metal [$m^2/g$] (MSA: metal surface area) or a carbon monoxide (CO) absorption per unit mass of the catalyst [ml/g (Cata.)].

When a gas phase reduction method using hydrogen as a reducing component is used, the conditions are not limited and the method can be performed by appropriately controlling the composition, temperature, and time of the reducing gas. Among the conditions, the reducing gas may be hydrogen alone but a mixed gas of hydrogen and nitrogen is preferably used and the composition [$H_2/(H_2+N_2)$] in volume is preferably 3/100 to 100/100, more preferably 5/100 to 30/100, and most preferably 10/100 to 20/100. With a too small amount of hydrogen, the reduction may be insufficient or the time required for the reduction may be prolonged. Note that a large ratio of hydrogen is unlikely to have a serious effect on the reduction of the precious metal component itself, but leads to an increased cost, and thus such a method may be unfavorable for industrial catalyst production.

The temperature in a gas phase reduction is preferably 100 to 500° C. and particularly preferably 200 to 400° C. At a too low temperature, the reduction may be insufficient or may require a long time, whereas at a too high temperature, sintering of the precious metal may occur to decrease the active surface area.

The time of the gas phase reduction is preferably 1 to 5 hours and more preferably 2 to 4 hours. With a too short reduction time, the reduction may be insufficient. In order to perform sufficient reduction in a short time, the temperature must be set to significantly high in some cases, which may cause sintering of the precious metal. With a too long reduction time, sintering of precious metal may also occur to decrease the active surface area.

A palladium-gold loaded catalyst for vinyl acetate synthesis can be obtained in the above manner. The loading positions of palladium and gold in this catalyst can be verified in the following manner.

Verification of the Same Width Load of Palladium and Gold (in the Case of Matching)

The production method of the present invention can provide a spherical VAM catalyst in which palladium and gold are biasedly present on the outer shell side of a spherical porous molded carrier and are loaded with significantly the same load widths. Such a state of the same load width can also be referred to as a matching state of palladium and gold. The verification method is not limited and the state can be verified by the degree of matching between the distribution peaks of palladium and gold, or by comparison between the load concentrations of palladium and gold in an arbitrary load width, or by comparison between the analyzed intensities of palladium and gold at a prescribed depth in the carrier using any analytical technique. Among them, in verification by analyzed intensities, the state can be represented by the coefficient of correlation.

The coefficient of correlation can be analyzed by a result of an elemental analysis by EPMA. Specifically, from characteristic X-ray intensities of Pd and Au obtained by an EPMA measurement, the coefficient of correlation R of distributions of Pd and Au in a particle is calculated by the following formula (1).

[Math. 1]

$$R = \frac{\sum_{i=1}^{n}(I_i(\text{Pd}) - \overline{I(\text{Pd})})(I_i(\text{Au}) - \overline{I(\text{Au})})}{\sqrt{\sum_{i=1}^{n}(I_i(\text{Pd}) - \overline{I(\text{Pd})})^2}\sqrt{\sum_{i=1}^{n}(I_i(\text{Au}) - \overline{I(\text{Au})})^2}} \quad (1)$$

In the formula (1), $I_i(\text{Pd})$ and $I_i(\text{Au})$ are X-ray intensities of palladium and gold obtained by an EPMA measurement, and the overlined I(Pd) and overlined I(Au) represent mean values of the intensities of each element.

The coefficient of correlation of palladium and gold in a VAM catalyst obtained by the production method of the present invention is preferably 0.6 or more, more preferably 0.7 or more, and most preferably 0.8 to 1.0. Then, in such a spherical porous molded carrier, 90% by weight or more of the total weight of palladium and gold is preferably present within 1 mm from the surface of the spherical porous molded carrier having a diameter as mentioned above, and more preferably within 0.5 mm.

Verification of Loading Positions of Palladium and Gold (in the Case of Biased Loading)

According to the production method of the present invention, a spherical VAM catalyst in which palladium and gold are present biasedly on the outer shell side of a spherical porous molded carrier and gold is loaded at a high concentration in the surface side of the catalyst and at a low concentration in the inside of the catalyst with respect to the load width of palladium can be obtained. This state can be considered as biased load of gold relative to palladium. The verification method of the state is not limited and the state can be verified by the degree of matching between the distribution peaks of palladium and gold, or by comparison between the load concentrations of palladium and gold in an arbitrary load width, or by comparison between the analyzed intensities of palladium and gold at a prescribed depth in a carrier using any analytical technique. Among them, in verification by analyzed intensities, the state can be represented by the intensity percentages of palladium and gold in a spherical porous molded carrier analyzed by EPMA.

A pretreatment of a sample was performed as follows: a spherical porous molded carrier particle was embedded in an epoxy resin, which was then polished such that the spherical porous molded carrier particle had a half size to expose a catalyst cross section, and carbon was deposited thereon. An electron probe microanalyzer JXA-8100 manufactured by JEOL was used for the measurement. The measurement was performed under conditions of an acceleration voltage of 15 KV, an irradiation current of 0.03 μA, and a stepping width of 1.5 μm. As a detector, a wavelength dispersion type detector was used.

A linear analysis was conducted through the center of the catalyst particle using the electron beam microanalyzer. When loading positions of palladium and gold are specified by the intensity percentages in the present invention, the depth in which 99.5% (this is referred to as an intensity percentage of a palladium component) or more is present relative to the sum total of intensities of the palladium component present from the outer surface to the center of the carrier is taken as a loading layer thickness W (mm). Note that in order to remove blank measurement points where palladium is not present, points having an intensity of 2 or more were extracted. Note that gold has low intensities and thus no measurement point was removed.

According to the results of such analyses, a VAM catalyst obtained by the production method of the present invention preferably has a ratio (Au 0.3 W/Pd 0.3 W) of the intensity percentage of the gold component (Au 0.3 W) to the intensity percentage of the palladium component (Pd 0.3 W) present in the depth of W×0.3 (mm) from the outer surface of the spherical porous molded carrier of 1.1 to 5.0, more preferably 1.2 to 4.0, and particularly preferably 1.5 to 3.0.

Additional Step

The production method of the present invention may have an additional step(s) in addition to the aforementioned steps. The additional steps include: a washing treatment after the immobilization of palladium and gold in an outer shell side of a spherical porous molded carrier through impregnation with an aqueous alkaline solution or after the reduction step; and impregnation load with another co-catalyst component.

Additional Step: Impregnation with Potassium Acetate

Among such additional steps, an example of impregnation with a co-catalyst component is impregnation with potassium acetate which is known in a catalytic reaction for obtaining VAM. The impregnation with potassium acetate in the present invention is preferably achieved by impregnating a spherical porous molded carrier after the reduction treatment with an aqueous potassium acetate solution. The amount of potassium acetate used is not limited and the amount of potassium acetate loaded per unit volume of the spherical porous molded carrier is preferably 25 [g/L] or more and more preferably 30 [g/L] or more. Since potassium acetate used in the present invention is also preferably evenly loaded in a carrier, potassium acetate is desirably loaded by impregnating a spherical porous molded carrier with an aqueous potassium acetate solution in an amount of 0.9 to 1 times the amount of saturated water absorption of the spherical porous molded carrier and drying the obtained carrier. Note that it is known that potassium acetate is supplied to the catalyst also in a VAM production process because it flows out in a vinyl acetate production process (PTL 3, NPL 2).

Catalyst Component Composition

When palladium, gold, and potassium are loaded on a VAM catalyst obtained by the production method of the present invention, the ratio by mass of the elements [palladium:gold:potassium] is not limited and is appropriately adjusted according to the load state, but is preferably [1:0.01 to 2:0.1 to 50] and more preferably [1:0.3 to 0.8:0.5 to 20].

A VAM catalyst obtained by the production method of the present invention has a shell structure in which palladium and gold are mostly loaded in the surface portion of a carrier (also referred to as egg shell structure). Although the shell structure is different depending on the conditions required according to the environment of use of the VAM catalyst, when a carrier having a diameter as described above is used in the production method of the present invention, a catalyst that has a thickness of a shell portion including a layer rich in gold and a palladium-loaded layer in the range of 0.1 to 0.5 mm can provide excellent performance.

A VAM catalyst obtained by the production method of the present invention is used for vinyl acetate synthesis. The use conditions of the VAM catalyst are not limited and may be appropriately adjusted based on conventionally known conditions. A known example is conditions in which a reaction temperature is 140 to 190° C., a reaction pressure is 6.5 to 8.7 [atoms], a composition ratio of the reactants (ethylene:oxygen:acetic acid (by volume)) is 63 to 73:7:20 to 30, and a space velocity is 1000 to 4000 [/h] (NPL 1). Since the VAM catalyst of the present invention has an action of buffering excess oxygen in the catalyst, the catalyst is preferably used in an environment having a high partial pressure of oxygen among the conventional conditions.

EXAMPLES

Examples of the present invention will be described below, but the present invention is not to be limited to the Examples and can be implemented within the scope of the present invention.

Example 1

Preparation of VAM Catalyst (1):

A catalyst was prepared according to the following procedure using a silica spherical carrier (diameter: 5.5 [mm], specific surface area: 154 [m$^2$/g], density at loading: 559 [g/L], saturated water absorption: 0.61 [g/g]).

A mixed solution of an aqueous $Na_2[PdCl_4]$ solution and an aqueous $H[AuCl_4]$ solution containing 4.1 g of metallic palladium and 2.1 g of metallic gold was provided for 1 L of a silica spherical carrier and was diluted with pure water so as to give the amount of saturated water absorption of the silica spherical carrier which was previously determined. The diluted solution was absorbed by 1 L of the silica spherical carrier to load the palladium compound and gold compound on the carrier. 36.3 g of $Na_2SiO_3 \cdot 9H_2O$ was dissolved in pure water to give a liquid volume of 460 mL. The palladium compound and gold compound-loaded silica spherical carrier was added to the aqueous solution and was immersed therein at room temperature for 16 hours or more to achieve precipitation of the palladium compound and the gold compound (immobilization on the carrier).

Then, the silica spherical carrier on which precipitation of the palladium compound and the gold compound was completed was taken out of the solution, and was immediately dried in an atmosphere at 100° C. without aging (moisture content: 7% by weight). The silica spherical carrier having a moisture content of 7% by weight was placed in a hydrogen reduction furnace at room temperature within 10 hours after drying, and gas phase reduction was conducted under hydrogen-containing gas flow at 300° C. for 3 hours. The silica carrier after the reduction treatment was taken out and was washed with pure water until the washing liquid was no longer clouded on dropping of a silver nitrate solution, followed by drying at 100° C., thereby obtaining a Pd—Au-loaded silica carrier.

Figure 1:
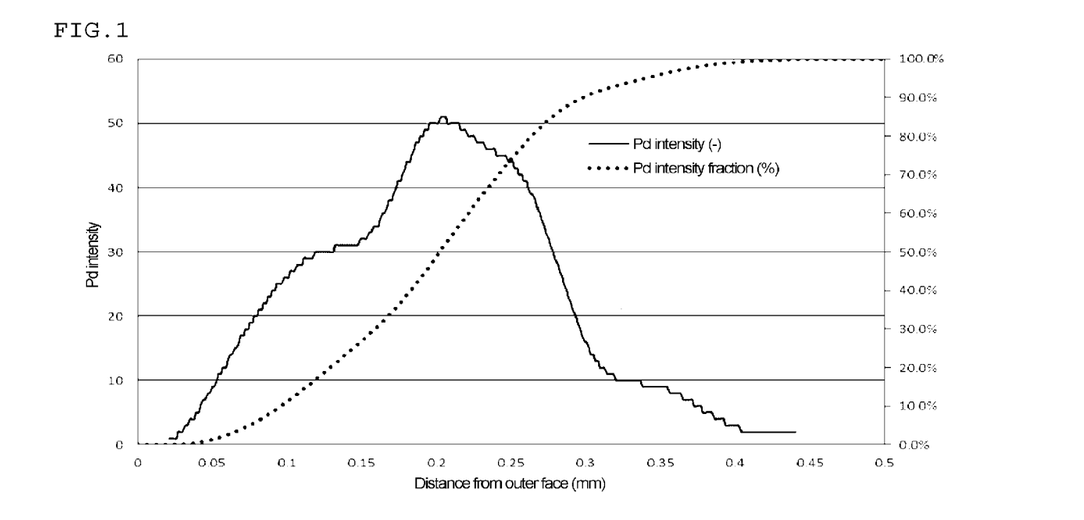
FIG. 1 It is a chart representing an intensity distribution of palladium from a catalyst surface, which is a result of a linear analysis by EPMA (electron probe micro analyzer) of palladium distribution in a catalyst of Example 1.
Figure 2:
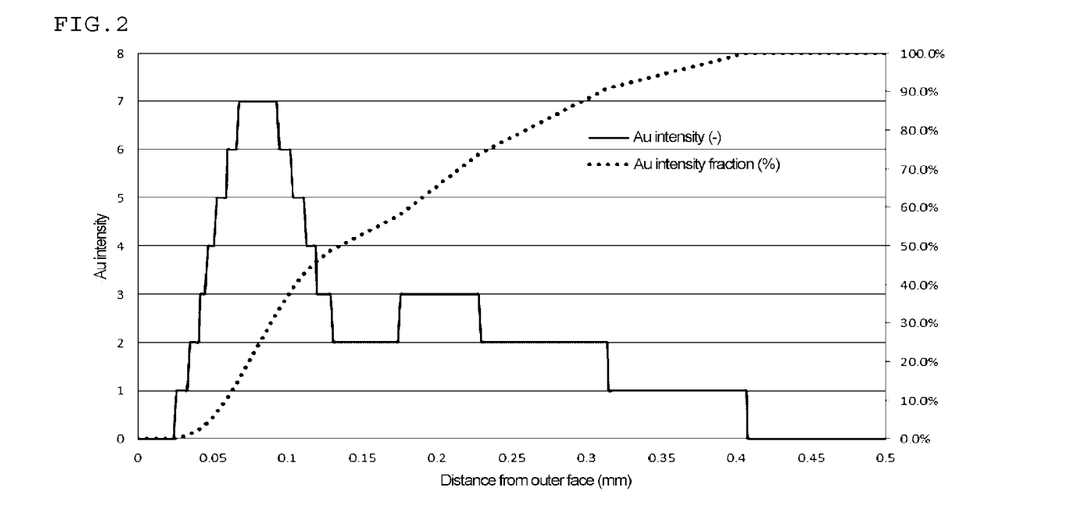
FIG. 2 It is a chart representing an intensity distribution of gold from the catalyst surface, which is a result of a linear analysis by EPMA of gold distribution in the catalyst of Example 1.

A pretreatment of a sample was performed as follows: a catalyst particle of the thus-obtained VAM catalyst was embedded in an epoxy resin, which was then polished such that the catalyst particle had a half size to expose a catalyst cross section, and carbon was deposited thereon. An elemental analysis was performed on the catalyst particle obtained after the sample treatment using EPMA (electron probe microanalyzer JXA-8100) manufactured by JEOL under conditions of an acceleration voltage of 15 KV, an irradiation current of 0.03 µA, and a stepping width of 1.5 µm. As a detector, a wavelength dispersion type detector was used. The intensity distribution and the intensity percentage of palladium in a depth of 0.5 mm from the surface layer side of the catalyst are shown in FIG. 1 by a solid line and a dotted line, respectively. Note that the intensity percentage corresponds to the total amount of palladium at each measurement point based on the surface side of the catalyst. Then, as with the case of the EPMA analysis of palladium, the intensity distribution and the intensity percentage of gold are shown in FIG. 2 by a solid line and a dotted line, respectively. It can be seen from the results of FIG. 1 and FIG. 2 that, with respect to palladium in the VAM catalyst of Example 1, gold is biasedly loaded on the surface side of the VAM catalyst.

Figure 3:
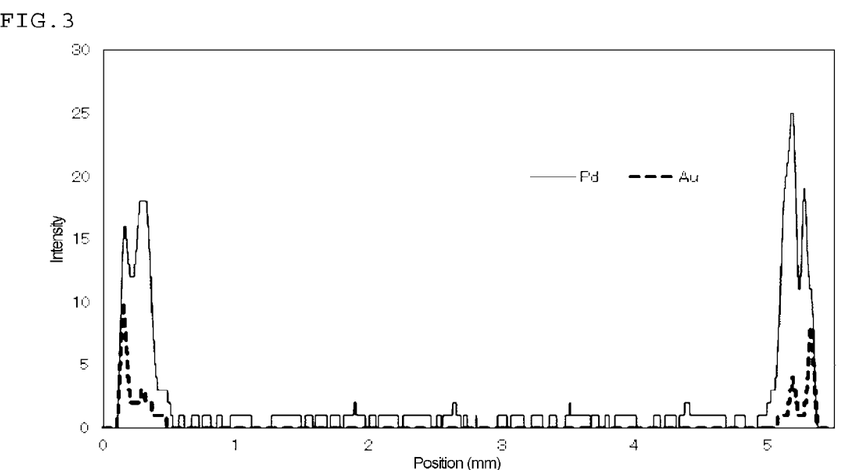
FIG. 3 It is a chart representing that the distributions of palladium and gold cannot be matched, which is a result of a linear analysis by EPMA (electron probe micro analyzer) of the catalyst of Example 1 which was obtained without an aging step.

In addition, the ratio of intensity percentages of palladium and gold (Au 0.3 W/Pd 0.3 W) was determined in the manner as described above. Then, the VAM catalyst of Example 1 had such a ratio of 2.54. Furthermore, the result of a linear analysis by an elemental analysis is shown in FIG. 3. The coefficient of correlation was determined here according to the procedure represented by the formula 1 as described above to be 0.486.

It was found from the above result that the degree of matching of palladium and gold in the VAM catalyst was low.

Example 2

Figure 4:
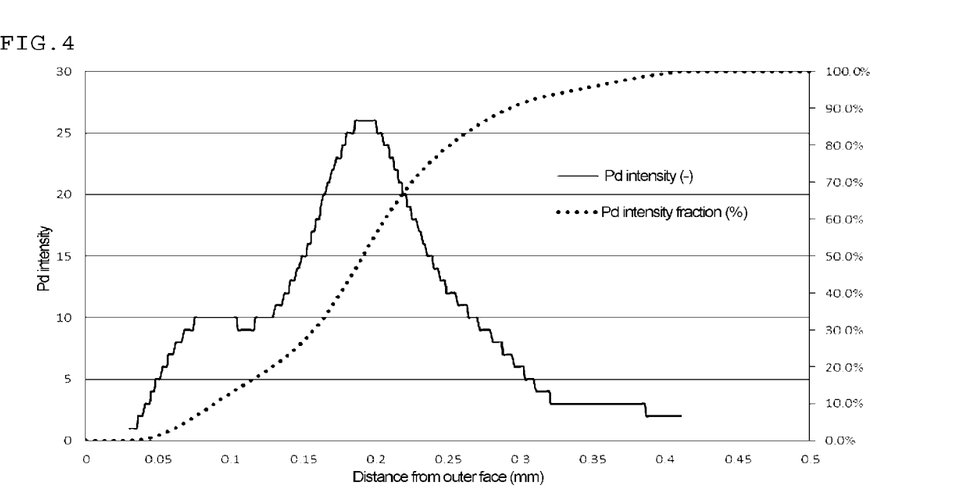
FIG. 4 It is a chart representing an intensity distribution of palladium from a catalyst surface, which is a result of a linear analysis by EPMA of a catalyst obtained in Example 2.
Figure 5:
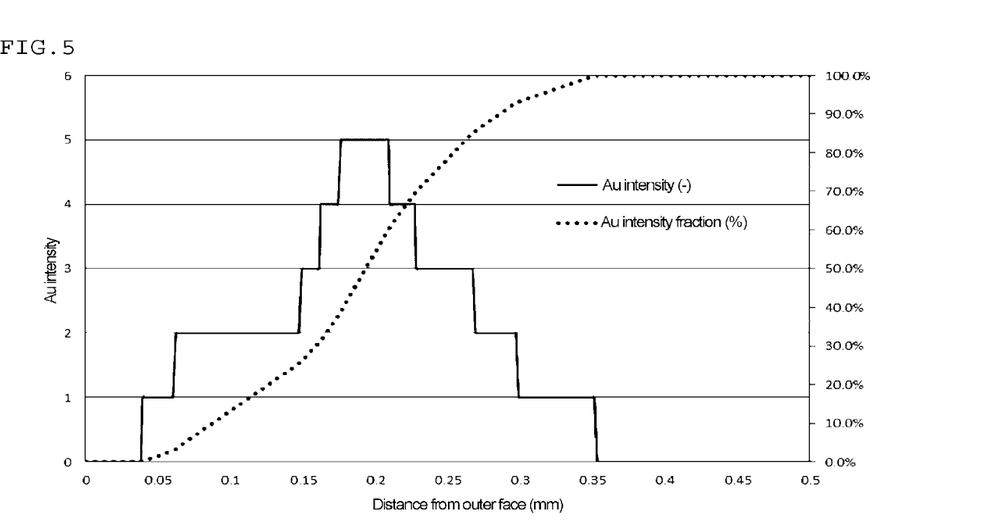
FIG. 5 It is a chart representing an intensity distribution of gold from the catalyst surface, which is a result of a linear analysis by EPMA of the catalyst obtained in Example 2.

Preparation of VAM Catalyst (2):

A VAM catalyst was obtained in the same manner as in Example 1 except that aging as described below was performed before the reduction treatment. As with Example 1, after precipitation of the palladium compound and the gold compound, the silica spherical carrier in which the precipitation of the palladium compound and the gold compound was completed was taken out from the solution and was dried in the atmosphere at 100° C. so that the moisture content became 7% by weight. The palladium compound and gold compound-loaded silica spherical carrier having a moisture content of 7% by weight was placed in a sealed container and was subjected to ageing at 60° C. for 7 days. The intensity distributions and the intensity percentages of palladium and gold are shown in FIGS. 4 and 5 as with Example 1. It was found that the load state of gold in the VAM catalyst of Example 2 was matched with the load state in the load width of palladium.

Figure 6:
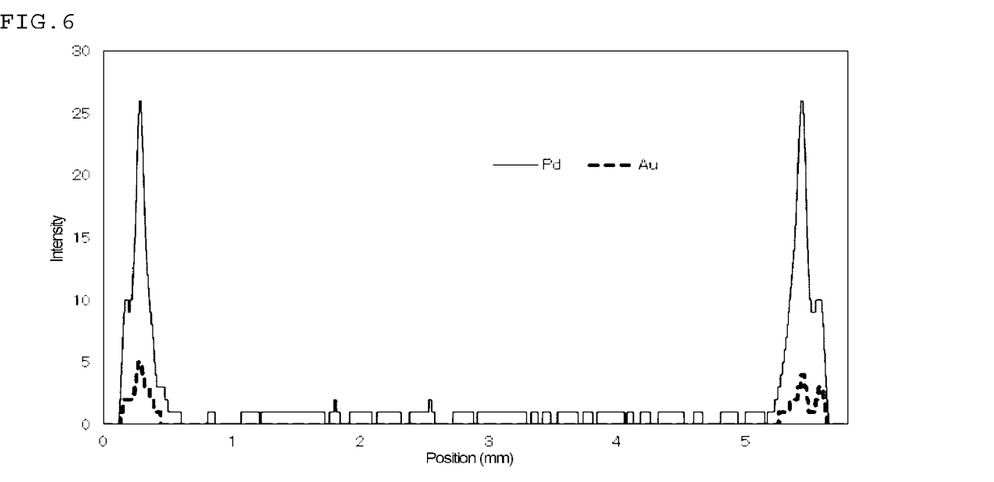
FIG. 6 It is a chart representing that the distributions of palladium and gold are matched, which is a result of a linear analysis by EPMA of the catalyst obtained in Example 2.

The intensity percentage in the VAM catalyst of Example 2 was determined in the same manner as in Example 1 to be 1.04 and the degree of matching of palladium and gold was high. In addition, the result of a linear analysis by an elemental analysis is shown in FIG. 6. The coefficient of correlation was determined here by the procedure represented by the formula 1 as described above to be 0.911.

It was found from the above result that the degree of matching of palladium and gold in the VAM catalyst was high.

Example 3

Preparation of VAM Catalyst (3):

A VAM catalyst was obtained in the same manner as in Example 1 except that aging as described below is performed before the reduction treatment. The silica spherical carrier in which precipitation of the palladium compound and the gold compound was completed was dried in the atmosphere at 100° C. and then a part of the sample was dried in the atmosphere at 105° C. for 8 hours. Then, a weight reduction of 2% by weight was observed and thus the moisture content in the palladium compound and gold compound-loaded silica spherical carrier was 2% by weight. The palladium compound and gold compound-loaded silica spherical carrier having a moisture content of 2% by weight was placed in a sealed container and was subjected to aging at 60° C. for 7 days. The carrier after aging was dried in the atmosphere at 100° C. and then was subjected to the reduction treatment and the subsequent steps in the same manner as in Example 1, thereby obtaining a VAM catalyst.

Figure 7:
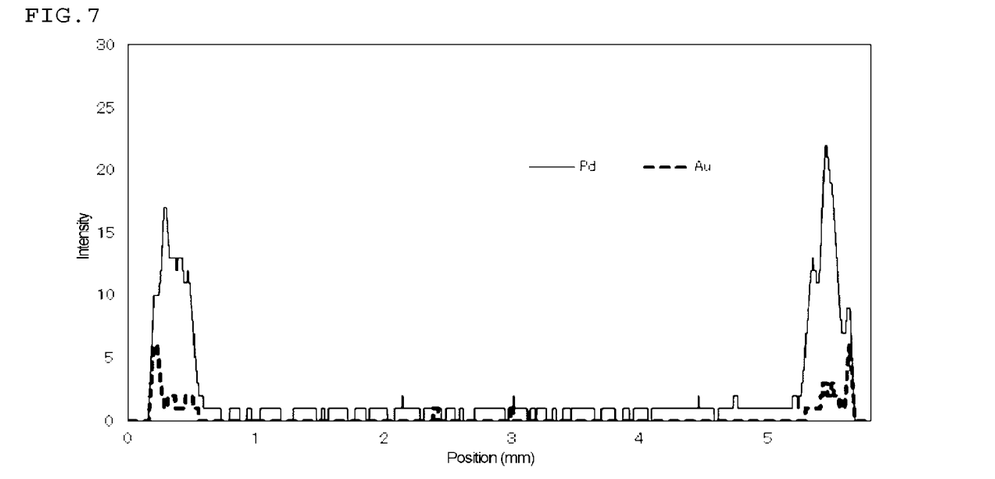
FIG. 7 It is a chart representing that the distributions of palladium and gold cannot be not matched, which is a result of a linear analysis by EPMA of a catalyst of Example 3 which was obtained with a low moisture content.

The obtained catalyst was subjected to an elemental analysis in the same manner as in Example 1. The result of a linear analysis is shown in FIG. 7. The coefficient of correlation was determined in the same manner as in Example 1 to be 0.535 and it was found that the degree of matching of palladium and gold was low.

Example 4

Preparation of VAM Catalyst (4):

Water corresponding to 30% by weight was supplied by spraying onto the palladium compound and gold compound-loaded silica spherical carrier having a moisture content of 2% by weight in Example 3 to obtain a palladium compound and gold compound-loaded silica spherical carrier having a moisture content of 32% by weight. This carrier was placed in a sealed container and was subjected to aging at 60° C. for 7 days, followed by the same procedure as in Example 2, thereby obtaining a VAM catalyst.

Figure 8:
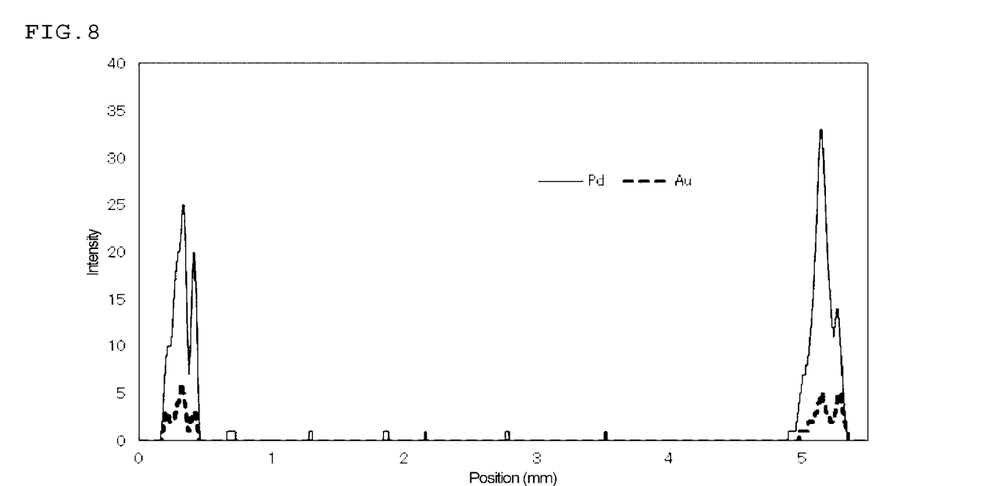
FIG. 8 It is a chart representing that the distributions of palladium and gold are matched, which is a result of a linear analysis by EPMA of a catalyst obtained in Example 4.

The obtained catalyst was subjected to an elemental analysis by the same manner as in Example 1. The result of a linear analysis is shown in FIG. 8. The coefficient of correlation was determined in the same manner as in Example 1 to be 0.864 and it was found that the degree of matching of palladium and gold was high.

INDUSTRIAL APPLICABILITY

According to the present invention, a catalyst for vinyl acetate production that is excellent in conversion and selectivity can be provided, which is useful in industry.

The invention claimed is:

1. A method of producing a palladium-gold loaded catalyst for vinyl acetate synthesis, the method comprising:
   (i) impregnating a spherical porous molded carrier formed of an inorganic oxide with a mixed aqueous solution that contains a palladium precursor serving as a catalytically active species and a gold precursor serving as a co-catalyst component, and subsequently impregnating the resultant spherical porous molded carrier with an aqueous alkaline solution to thereby water-insolubilize the palladium precursor and the gold precursor in the spherical porous molded carrier, thus obtaining a palladium-gold immobilized spherical porous molded carrier; and
   (ii) subsequently adjusting a moisture content of the palladium-gold immobilized spherical porous molded carrier to 4% or more by weight based on the total weight of the palladium-gold immobilized spherical porous molded carrier, and
   (iii) aging the adjusted palladium-gold immobilized spherical porous molded carrier while a moisture content of the adjusted palladium-gold immobilized spherical porous molded carrier is maintained at 4% or more by weight at 40° C. or more for 72 hours or more.

2. The method according to claim 1, wherein the spherical porous molded carrier has:
   a diameter of 3 to 7 mm,
   a specific surface area of 10 to 1000 m$^2$/g, and
   a saturated water absorption of 0.2 to 2 g/g.

3. The method according to claim 1, further comprising:
   after (iii), reducing the palladium-gold immobilized spherical porous molded carrier.

4. The method according to claim 1, wherein in (iii), the aging is performed at 40 to 120° C. for 72 hours or more.

5. The method according to claim 1, wherein water vaporization from the adjusted palladium-gold immobilized spherical porous molded carrier is suppressed during the aging.

6. The method according to claim 1, wherein the aging is in a sealed container.

7. The method according to claim 1, wherein the aging forms a palladium-gold immobilized spherical porous molded carrier on which distributions of gold and palladium have a correlation coefficient of 0.8 to 1.0.

8. The method according to claim 1, wherein the aging forms a palladium-gold immobilized spherical porous molded carrier on which 90% by weight or more of a total weight of palladium and gold is present within 1 mm from the surface of the palladium-gold immobilized spherical porous molded carrier.

* * * * *